(12) United States Patent
Briggs et al.

(10) Patent No.: US 7,485,759 B2
(45) Date of Patent: *Feb. 3, 2009

(54) MINIMIZATION OF LIGAND DEGRADATION PRODUCTS, OR REVERSION OF SAME TO USEFUL PHOSPHINE LIGANDS

(75) Inventors: John R. Briggs, Midland, MI (US); Wei-Jun Peng, Midland, MI (US); Brian M. Roesch, Middletown, DE (US); Anthony G. Abatjoglou, Charleston, WV (US); Donald L. Morrison, Fort Collins, CO (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/018,841

(22) Filed: Jan. 24, 2008

(65) Prior Publication Data
US 2008/0114191 A1 May 15, 2008

Related U.S. Application Data

(63) Continuation of application No. 10/562,602, filed as application No. PCT/US2004/020813 on Jun. 28, 2004, now Pat. No. 7,351,868.

(60) Provisional application No. 60/484,807, filed on Jul. 3, 2003.

(51) Int. Cl.
C07C 45/50 (2006.01)
(52) U.S. Cl. ..................................... 568/451; 568/454
(58) Field of Classification Search .................. 568/451, 568/454
See application file for complete search history.

(56) References Cited

U.S. PATENT DOCUMENTS

| | | | |
|---|---|---|---|
| 3,527,809 A | 9/1970 | Pruett et al. | |
| 4,148,830 A | 4/1979 | Pruett et al. | |
| 4,269,781 A | 5/1981 | Vanderspurt et al. | |
| 4,283,562 A | 8/1981 | Billig et al. | |
| 4,400,548 A | 8/1983 | Abatjoglou et al. | |
| 4,593,127 A | 6/1986 | Bunning et al. | |
| 4,717,775 A | 1/1988 | Billig et al. | |
| 4,769,498 A | 9/1988 | Billig et al. | |
| 4,774,361 A | 9/1988 | Maher et al. | |
| 4,885,401 A | 12/1989 | Billig et al. | |
| 5,180,854 A | 1/1993 | Abatjoglou et al. | |
| 5,264,616 A | 11/1993 | Roeper et al. | |
| 5,288,918 A | 2/1994 | Maher | |
| 5,360,938 A | 11/1994 | Babin et al. | |
| 5,364,950 A | 11/1994 | Babin et al. | |
| 5,491,266 A | 2/1996 | Babin et al. | |
| 5,495,041 A | 2/1996 | Sielcken et al. | |
| 5,693,851 A | 12/1997 | Sielcken et al. | |
| 5,741,945 A | 4/1998 | Bryant et al. | |
| 5,886,237 A | 3/1999 | Packett et al. | |
| 6,034,286 A | 3/2000 | Guram et al. | |
| 6,191,324 B1 | 2/2001 | Guram et al. | |
| 6,294,700 B1 | 9/2001 | Kanel et al. | |
| 6,303,829 B1 | 10/2001 | Kanel et al. | |
| 6,369,283 B1 | 4/2002 | Guram et al. | |
| 7,351,868 B2 * | 4/2008 | Briggs et al. ................. 568/451 |
| 2002/0007096 A1 | 1/2002 | Packett et al. | |
| 2002/0183196 A1 | 12/2002 | Yada et al. | |
| 2006/0058557 A1 | 3/2006 | Peng et al. | |
| 2006/0100453 A1 | 5/2006 | Peng et al. | |
| 2006/0193802 A1 | 8/2006 | Lysenko et al. | |

FOREIGN PATENT DOCUMENTS

| | | |
|---|---|---|
| EP | 0518241 B1 | 9/1996 |
| EP | 1249455 A1 | 10/2002 |
| WO | WO 03/078444 A3 | 9/2003 |
| WO | WO 2004/096744 A3 | 11/2004 |
| WO | WO 2007/133379 A1 | 11/2007 |

OTHER PUBLICATIONS

A. Benyei et al., "The Effect of Phosphonium Salt Formation on the Kinetics of Homogeneous Hydrogenations in Water Utilizing a Rhodium Meta-Sulfonatophenyl-Diphenylphosphine Complex", *Journal of Molecular Catalysis*, (1993) 84, 157-163.

Malcolm A. Shaw et al., "Addition Reactions of Tertiary Phosphorus Compounds with Electrophilic Olefins and Acetylenes," *Topics in Phosphorus Chemistry*, (1972) 7, 1-35.

(Continued)

*Primary Examiner*—Sikarl A Witherspoon
(74) *Attorney, Agent, or Firm*—Marie F. Zuckerman

(57) ABSTRACT

A process for the minimization of phosphonium ion ligand degradation products formed during reaction of a polyunsaturated olefin or an unconjugated functionalized olefin in the presence of a transition metal-triorganophosphine ligand complex catalyst to form as a product, by-product, or intermediate product a conjugated functionalized olefin having a carbon-carbon double bond conjugated to an α-electron-withdrawing group, such as, an α,β-unsaturated aldehyde, ketone, ester, acid, or nitrile. The minimization process involves conducting the reaction under selected conditions of conversion, temperature, pressure, or a combination thereof; and/or by selecting a triorganophosphine ligand with a specified steric and/or electronic property. Further, a process for reversion of phosphonium ion ligand degradation product(s) back to useful triorganophosphine ligand(s), the reversion involving treating a reaction product fluid containing the degradation product(s) with an inert gas, hydrogen, synthesis gas, or a mixture thereof under conditions sufficient to regenerate the triorganophosphine ligand(s).

12 Claims, No Drawings

OTHER PUBLICATIONS

WM. A. Henderson, Jr. et al., "The Nucleophilicity of Phosphines", *Journal of the American Chemical Society*, (1960) 82, 5794-5800.

Chadwick A. Tolman, "Steric Effects of Phosphorus Ligands in Organometallic Chemistry and Homogeneous Catalysis," *Chemical Reviews*, (1977) 77(3), 318-348.

MD. Matiur Rahman, et al., "Separation of Phosphorus (III) Ligands into Pure σ-Donors and σ-Donor/π-Acceptors: Comparison of Basicity and σ-Donicity[1]", *Organometallics*, (1989) 8(1), 1-7.

WM. A Henderson, Jr. et al., "The Basicity of Phosphines", *Journal of the American Chemical Society*, (1960) 82, 5791-5794.

Tim Allman et al., "The Basicity of Phosphines", *Canadian Journal of Chemistry* (1982) 60(6), 716-722.

Fenton, et al., "Influence of Poles and Polar Linkings on the Course Pursued by Elimination Reactions. Part V. The Mechanism of Thermal Decomposition of Quarternary Phosphonium Hydroxides," *Journal of the Chemical Society*, Part 2, (1929), 2342-2357; (Best Copy Available); includes Chemical Abstract.

* cited by examiner

MINIMIZATION OF LIGAND DEGRADATION PRODUCTS, OR REVERSION OF SAME TO USEFUL PHOSPHINE LIGANDS

CROSS REFERENCE TO RELATED APPLICATIONS

This application is a continuation of U.S. patent application Ser. No. 10/562,602, filed Dec. 28, 2005 now U.S. Pat. No. 7,351,868, which is a 371 of International Patent Application PCT/US2004/020813, filed Jun. 28, 2004, which claims the benefit of U.S. Provisional Patent Application Ser. No. 60/484,807, filed Jul. 3, 2003.

BACKGROUND OF THE INVENTION

In one aspect, this invention pertains to a method of minimizing phosphonium ion ligand degradation products that are formed in a reaction of a polyolefin in the presence of a transition metal-triorganophosphine ligand complex catalyst to yield as a product, by-product, or intermediate product a conjugated functionalized olefin. As used herein, the term "polyolefin," or its equivalent "polyunsaturated olefin," refers to an olefin having a plurality of unsaturated carbon-carbon double bonds. The term "conjugated functionalized olefin" shall refer herein to a compound comprising a carbon-carbon double bond conjugated to an $\alpha$-electron-withdrawing group, such as an aldehyde, ketone, ester, acid, or nitrile. As an example, this invention pertains to a method of minimizing the formation of phosphonium ion ligand degradation products that are formed in the hydroformylation of a polyolefin with carbon monoxide in the presence of hydrogen and a transition metal-triorganophosphine ligand complex catalyst to produce an $\alpha,\beta$-unsaturated aldehyde.

In a second aspect, this invention pertains to a process of minimizing phosphonium ion ligand degradation products that are formed in a reaction of an unconjugated functionalized olefin, such as an unconjugated unsaturated ester, in the presence of a transition metal-triorganophosphine ligand complex catalyst, to form as a product, by-product, or intermediate product a conjugated functionalized olefin, such as an $\alpha,\beta$-unsaturated ester. Isomerization reactions exemplify this type of reaction.

In a third aspect, this invention pertains to a process for the reversion of phosphonium ion ligand degradation products back to useful triorganophosphine ligands.

Processes catalyzed by transition metal-triorganophosphine ligand complex catalysts are described in the prior art, for example, in the following: U.S. Pat. Nos. 6,369,283, 6,191,324, 5,886,237, 5,693,851, and 5,495,041. Such useful processes include hydroformylation, hydroacylation, hydroesterification, carbonylation, and hydrocyanation. The products of these reactions include, for example, aldehydes, ketones, esters, acids, and nitriles, respectively, which find widespread utility in the chemical industry.

The prior art, as illustrated by U.S. Pat. No. 6,191,324, discloses a carbonylation process wherein a polyunsaturated olefin, such as butadiene, is hydroformylated with carbon monoxide in the presence of hydrogen and a hydroformylation catalyst comprising a Group VIII transition metal-triorganophosphine ligand complex catalyst, to form an unsaturated aldehyde. The polyunsaturated olefin conversion may range from about 27 up to 99 percent. Disadvantageously, the use of polyunsaturated olefin presents a problem not encountered when a monounsaturated olefin is used, namely, that the rate of triorganophosphine ligand usage can exceed an acceptable level. As a consequence, ligand degradation products form in unacceptable yield. The loss of useful ligand may disadvantageously reduce catalyst activity. Moreover, make-up ligand must be added to the process to maintain catalytic activity and to prevent catalytic metal from depositing out of the reaction fluid. The economic disadvantages resulting from ligand loss, reduced catalyst activity, and the need for make-up ligand diminish the prospects for commercializing polyunsaturated olefins as reactants in such processes. As a further disadvantage, the ligand degradation products themselves may be sufficiently basic to catalyze the formation of undesirable heavies with accompanying losses in selectivity and yield to desired products. Heavies by-products also necessitate additional separation and purification efforts, if desired products of acceptable purity are to be obtained.

Certain academic and patent publications disclose the reactions of activated olefins with triorganophosphines to form zwitter-ionic phosphonium salts. See for example, A. Bényei et al., *Journal of Molecular Catalysis*, 84 (1993), 157-163; and M. A. Shaw and R. S. Ward, "Addition Reactions of Tertiary Phosphorus Compounds with Electrophilic Olefins and Acetylenes," Topics in Phosphorus Chemistry, 7 (1972), 1-35, as well as US-A1-2002/0183196 and EP-A1-1,249, 455. Such publications may suggest that the ligand degradation products formed during reactions of polyunsaturated olefins in the presence of triorganophosphine ligands might also comprise zwitter-ionic phosphonium salts.

Reference is also made to co-pending International Patent Application Serial No. PCT/US04/012246, entitled "Aldehyde and Alcohol Compositions Derived from Seed Oils," filed on Apr. 22, 2004, in the names of Zenon Lysenko et al., which discloses the hydroformylation of polyunsaturated olefins derived from seed oils in the presence of transition metal-organophosphorus ligand complex catalysts for the purpose of preparing specific compositions of mono-, di-, and tri-formylated fatty acid esters. This international patent application does not recognize the problem of organophosphine ligand loss to phosphonium ion degradation products or any solution to such a problem.

In view of the above, it would be desirable to discover a process that minimizes formation of ligand degradation product(s) during reaction of a polyolefin in the presence of a transition metal-triorganophosphine ligand complex catalyst to form as an product, by-product, or intermediate product a compound having a carbon-carbon double bond conjugated to an $\alpha$-electron-withdrawing group, such as aldehyde, ketone, ester, acid, or nitrile. It would be more desirable if such a minimization process could be implemented easily and at reasonable cost. Discovery of such a minimization process would reduce the loss of catalytic metal and the need for make-up ligand; would provide for more consistent catalyst activity; and would reduce the production of heavies and the problems associated therewith. Additionally, it would be desirable to discover a process that reverts phosphonium ion ligand degradation products, once formed and present in reaction product fluids, back to useful triorganophosphine ligands. Such a reversion process would beneficially remove phosphonium ion ligand degradation products from reaction product fluids, conserve useful ligands, and reduce the detrimental effects such ligand degradation products produce.

SUMMARY OF THE INVENTION

In one aspect, this invention provides for a novel method of minimizing the production of a phosphonium ion ligand degradation product, or mixture of such products, in a process comprising the reaction of a polyunsaturated olefin in the presence of a transition metal-triorganophosphine ligand complex catalyst to form as a product, by-product, or intermediate product a compound having a carbon-carbon double bond conjugated to an α-electron-withdrawing group. As noted hereinabove, the compound characterized by the carbon-carbon double bond conjugated to an α-electron-withdrawing group will be hereinafter referred to as the "conjugated functionalized olefin." Moreover, for the purposes of this invention, the phosphonium ion ligand degradation product shall comprise an adduct or reaction product of a triorganophosphine ligand and the conjugated functionalized olefin. In such a process comprising reaction of a polyunsaturated olefin in the presence of a transition metal-triorganophosphine ligand complex catalyst to form as a product, by-product, or intermediate product a conjugated functionalized olefin, the method to minimize the phosphonium ion ligand degradation product or mixture of such products comprises (a) employing in the reaction process a triorganophosphine ligand having a steric or electronic property, or a combination thereof, sufficient to minimize production of phosphonium ion ligand degradation product(s); or (b) conducting the reaction process to a polyunsaturated olefin conversion, or at a temperature, or at a pressure, or at a combination of said process conditions sufficient to minimize the formation of ligand degradation product(s); or (c) conducting the process by combining a method of (a) with a method of (b).

In a second aspect, this invention provides for a novel method of minimizing the production of a phosphonium ion ligand degradation product, or mixture of such products, in a process comprising reaction of an unconjugated functionalized olefin in the presence of a transition metal-triorganophosphine ligand complex catalyst to form as a product, by-product, or intermediate product a conjugated functionalized olefin. In the following description, the unconjugated functionalized olefin comprises at least one carbon-carbon double bond in an unconjugated position relative to an α-electron-withdrawing group. In such a process comprising the reaction of an unconjugated functionalized olefin in the presence of a transition metal-triorganophosphine ligand complex catalyst to form as a product, by-product, or intermediate product a conjugated functionalized olefin, the method to minimize the phosphonium ion ligand degradation product or mixture of such products comprises (a) employing in the reaction process a triorganophosphine ligand having a steric or electronic property, or a combination thereof, sufficient to minimize production of phosphonium ion ligand degradation product(s); or (b) conducting the reaction process to an unconjugated functionalized olefin conversion, or at a temperature, or at a pressure, or at a combination of said process conditions sufficient to minimize the formation of ligand degradation product(s); or (c) conducting the process by combining a method of (a) with a method of (b).

In a third aspect, this invention provides for a novel process for reversion of a phosphonium ion ligand degradation product or a mixture of such products back to useful triorganophosphine ligand or mixture of such ligands. The novel reversion process of this invention comprises treating a reaction product fluid containing a phosphonium ion ligand degradation product or mixture of such products, which is capable of reversion to useful triorganophosphine ligand, with an inert gas, hydrogen, synthesis gas, or a mixture thereof, under conditions sufficient to revert the phosphonium ion ligand degradation product or mixture of products back to triorganophosphine ligand or mixture of such ligands.

As seen from the description hereinabove, in one manner the method of this invention advantageously minimizes the degradation and loss of useful triorganophosphine ligands to phosphonium ion ligand degradation products. In this context, the word "minimizes" shall be included to mean any degree of reduction, lessening, or lowering, including but not limited to reduction to the lowest achievable level. In another manner, the method of this invention advantageously reverts phosphonium ion ligand degradation products, already formed, back to useful triorganophosphine ligands. As a consequence, the methods of this invention advantageously conserve useful ligand, reduce the rate of ligand usage, reduce the loss of catalytic metal, minimize the need for make-up ligand, and conserve catalyst activity. Moreover, the methods of this invention advantageously minimize the formation of undesirable heavies by-products whose formation is catalyzed by phosphonium ion ligand degradation products.

In a fourth aspect, this invention provides for an integrated process for reaction of a polyunsaturated olefin comprising (a) contacting a polyunsaturated olefin with carbon monoxide, optionally in the presence of hydrogen, alcohol, or water, and in the presence of a transition metal-triorganophosphine ligand complex catalyst and free triorganophosphine ligand, under process conditions sufficient to prepare a reaction product fluid comprising a transition metal-triorganophosphine ligand complex catalyst, optionally free triorganophosphine ligand, one or more reaction products, by-products, and/or intermediate products including an α,β-unsaturated aldehyde, ketone, ester, or acid, and one or more phosphonium ion ligand degradation products capable of reversion to useful ligand; (b) treating the reaction product fluid of step (a) with an inert gas, hydrogen, synthesis gas, or a combination thereof, under conditions sufficient to revert the one or more phosphonium ion ligand degradation products back to triorganophosphine ligand; (c) feeding the reaction product fluid taken from step (b), now containing reduced amounts of phosphonium ion ligand degradation products, to a vaporizer or an extractor for separation into a first phase containing reaction products, by-products, and intermediate products and a second phase containing transition metal-triorganophosphine ligand complex catalyst and optionally free triorganophosphine ligand; and (d) recycling the second phase containing the transition metal-triorganophosphine ligand complex catalyst and optional free triorganophosphine ligand back to reaction process step (a).

In a fifth aspect, this invention provides for an integrated process for reaction of a polyunsaturated olefin comprising (a) contacting a polyunsaturated olefin with carbon monoxide, optionally in the presence of hydrogen, alcohol, or water, and in the presence of a transition metal-triorganophosphine ligand complex catalyst and free triorganophosphine ligand, under process conditions sufficient to prepare a reaction product fluid comprising a transition metal-triorganophosphine ligand complex catalyst, optionally free triorganophosphine ligand, one or more reaction products, by-products, and/or intermediate products including an α,β-unsaturated aldehyde, ketone, ester, or acid, and one or more phosphonium ion ligand degradation products capable of reversion back to useful ligand; (b) feeding the reaction product fluid from step (a) to a vaporizer or an extractor for separation into a first phase containing reaction products, by-products, and intermediate products, and a second phase containing transition metal-triorganophosphine ligand complex catalyst, optionally free triorganophosphine ligand, and one or more phosphonium ion ligand degradation products; (c) treating the second phase containing the transition metal-triorganophosphine ligand complex catalyst, optionally free triorganophosphine ligand, and phosphonium ion ligand degradation products with an inert gas, hydrogen, synthesis gas, or a combination thereof, under conditions sufficient to revert the phosphonium ion ligand degradation products back to triorganophosphine ligand; and (d) recycling the phase from step (c) containing the transition metal-triorganophosphine ligand complex catalyst and optional free triorganophosphine ligand, now containing reduced amounts of phosphonium ion ligand degradation products, back to reaction process step (a).

The aforementioned processes for reacting polyunsaturated olefins beneficially integrate basic carbonylation processes with methods for reverting phosphonium ion ligand degradation products back to useful ligands, and further, with methods for separating the catalyst and ligand from the reaction products, by-products, and intermediate products.

DETAILED DESCRIPTION

In view of the above, this invention provides in one aspect for a novel process of minimizing the production of one or more phosphonium ion ligand degradation products in a process wherein a polyolefin, hereinafter also referred to as a polyunsaturated olefin, is reacted in the presence of a transition metal-triorganophosphine ligand complex catalyst to form as a product, by-product, or intermediate product a conjugated functionalized olefin, that is, a compound characterized as having a carbon-carbon double bond conjugated to an α-electron-withdrawing group. The α-electron-withdrawing group may be, for example, an aldehyde, ketone, ester, acid (carboxylic acid), or nitrile. For the purposes of this invention, a phosphonium ion ligand degradation product shall comprise an adduct or a reaction product of a triorganophosphine ligand and the conjugated functionalized olefin. In such a reaction process, the minimization of phosphonium ion ligand degradation product or mixture of such products comprises (a) employing in the reaction process a triorganophosphine ligand having a steric or electronic property, or combination thereof, sufficient to minimize the formation of phosphonium ion ligand degradation product(s); or (b) conducting the reaction process to a polyunsaturated olefin conversion, or at a temperature, or at a pressure, or at a combination of said process conditions, sufficient to minimize the formation of ligand degradation product(s); or (c) conducting the process by combining a method of (a) with a method of (b).

In a related preferred aspect, this invention provides for a novel process of minimizing the production of one or more phosphonium ion ligand degradation products in a process wherein a $C_{4-60}$ polyene ($C_{4-60}$ polyunsaturated olefin) is contacted with carbon monoxide, optionally in the presence of hydrogen, alcohol, or water, the contacting being conducted in the presence of a transition metal-triorganophosphine ligand complex catalyst and free triorganophosphine ligand, to form as a product, by-product, or intermediate product a conjugated functionalized olefin, wherein the functionalized group is selected from aldehydes, ketones, esters, or acids. In this preferred process, the minimization of phosphonium ion ligand degradation product(s) comprises (a) employing in the carbonylation process a triorganophosphine ligand having a cone angle greater than about 135 degrees or a pKa less than about 8.3, or a combination thereof; or (b) conducting the carbonylation to a polyunsaturated olefin conversion greater than about 80 weight percent, preferably, greater than about 85 weight percent, and more preferably, greater than about 90 weight percent, but less than about 95 weight percent; or conducting the process at a temperature greater than about 45° C. and less than about 95° C., or at a pressure greater than about 300 psig (2,068 kPa) and less than about 5,000 psig (34.5 MPa), or at a combination of said process conditions; or (c) conducting the carbonylation process by combining a method of (a) with a method of (b).

In a second aspect, this invention provides for a novel method of minimizing the production of a phosphonium ion ligand degradation product, or mixture of such products, in a process comprising reaction of an unconjugated functionalized olefin in the presence of a transition metal-triorganophosphine ligand complex catalyst to form as a product, by-product, or intermediate product a conjugated functionalized olefin. As defined hereinbefore, the unconjugated functionalized olefin shall comprise at least one carbon-carbon double bond in an unconjugated position relative to an α-electron-withdrawing group, such as an aldehyde, ketone, ester, acid, or nitrile. The conjugated functionalized olefin, defined previously hereinbefore, places the carbon-carbon double bond and the α-electron-withdrawing group in conjugation. The minimization of phosphonium ion ligand degradation product or mixture of such products in such a process comprises (a) employing in the process a triorganophosphine ligand having a steric or electronic property, or combination thereof, sufficient to minimize the formation of phosphonium ion ligand degradation product(s); or (b) conducting the process to an unconjugated functionalized olefin conversion, or at a temperature, or at a pressure, or a combination of said process conditions sufficient to minimize the production of phosphonium ion ligand degradation product(s); or (c) combining a method of (a) with a method of (b).

In a preferred related aspect, this invention provides for a novel method of minimizing the production of a phosphonium ion ligand degradation product, or mixture of such products, in a process comprising isomerization of an unconjugated functionalized $C_{4-60}$ polyunsaturated olefin in the presence of a transition metal-triorganophosphine ligand complex catalyst to form as a product, by-product, or intermediate product a conjugated functionalized $C_{4-60}$ polyunsaturated olefin, wherein the aforementioned functionalizations are selected from aldehyde, ketone, ester, acid, and nitrile functionalities. In this preferred process, the minimization of phosphonium ion ligand degradation product(s) comprises (a) employing in the isomerization process a triorganophosphine ligand having a cone angle greater than about 135 degrees or a pKa less than about 8.3, or a combination thereof; or (b) conducting the isomerization to an unconjugated functionalized olefin conversion greater than about 80 weight percent, preferably, greater than about 85 weight percent, and more preferably, greater than about 90 weight percent, but less than about 95 weight percent; or conducting the isomerization at a temperature greater than about 45° C. and less than about 95° C., or at a pressure greater than about 300 psig (2,068 kPa) and less than about 5,000 psig (34.5 MPa), or at a combination of said process conditions; or (c) combining a method of (a) with a method of (b).

This invention, in another aspect, provides for a novel process for reversion of a phosphonium ion ligand degradation product or mixture of such products back to useful ligand or mixture of useful ligands. Such phosphonium ion ligand degradation products may be formed, for example, during processes wherein a polyunsaturated olefin is reacted in the presence of a transition metal-triorganophosphine ligand complex catalyst to form as a product, by-product, or intermediate product a conjugated functionalized olefin, as noted hereinabove. Alternatively, such degradation products may be formed during isomerization processes wherein an unconjugated functionalized olefin is isomerized to form the conjugated functionalized olefin. In this aspect, the novel reversion process comprises treating a reaction product fluid containing a phosphonium ion ligand degradation product or mixture of products, which is capable of reversion back to useful triorganophosphine ligand, with an inert gas, hydrogen, synthesis gas, or a combination thereof, under conditions sufficient to revert the phosphonium ion ligand degradation product or mixture of such products back to triorganophosphine ligand or mixture of such ligands.

In one related preferred embodiment, a novel process is provided for reversion of a phosphonium ion ligand degradation product capable of reversion to useful ligand, such degradation product comprising an adduct of a triorganophosphine ligand and a $C_{5-60}$ α,β-unsaturated aldehyde, acid, ester, ketone, or nitrile. The novel process comprises treating a reaction product fluid containing the phosphonium ion ligand degradation product or mixture of such products with an inert gas, hydrogen, synthesis gas, or a mixture thereof, under conditions sufficient to revert the phosphonium ion ligand degradation product or products back to useful triorganophosphine ligand or mixture of ligands.

In a more preferred embodiment, a novel process is provided for reversion of a phosphonium ion ligand degradation product comprising an adduct of a triorganophosphine ligand and pent-2-ene-1-al (hereinafter "2-pentenal"). In this aspect, the novel process comprises treating a reaction product fluid containing the phosphonium ion ligand degradation product with an inert gas under conditions sufficient to remove 2-pentenal. By removing 2-pentenal, preferably by volatilization with the inert gas, the phosphonium ion ligand degradation product reverts back to the useful triorganophosphine ligand.

In another more preferred embodiment, a novel process is provided for reversion of a phosphonium ion ligand degradation product comprising an adduct of a triorganophosphine ligand and 2-pentenal. The novel process comprises treating a reaction product fluid containing the phosphonium ion ligand degradation product with a source of synthesis gas under conditions sufficient to hydroformylate 2-pentenal. By removing 2-pentenal via hydroformylation, preferably to 2-formyl-pentanal and/or 3-formyl-pentanal, the phosphonium ion ligand degradation product reverts back to useful triorganophosphine ligand.

In another more preferred embodiment, a novel process is provided for reversion of a phosphonium ion ligand degradation product comprising an adduct of a triorganophosphine ligand and 2-pentenal. The novel process comprises treating a reaction product fluid containing the phosphonium ion ligand degradation product with a source of hydrogen under conditions sufficient to hydrogenate 2-pentenal. By removing 2-pentenal via hydrogenation, preferably to pentanal and/or pentanol, the phosphonium ion ligand degradation product reverts back to useful triorganophosphine ligand.

In another aspect, this invention provides for an integrated process for carbonylation of a polyunsaturated olefin comprising (a) contacting a polyunsaturated olefin with carbon monoxide, optionally, in the presence of hydrogen, alcohol, or water, and in the presence of a transition metal-triorganophosphine ligand complex catalyst and free triorganophosphine ligand, under process conditions sufficient to prepare a reaction product fluid comprising a transition metal-triorganophosphine ligand complex catalyst, optionally free triorganophosphine ligand, one or more reaction products, by-products, and/or intermediate products including an α,β-unsaturated aldehyde, ketone, ester, or acid, and one or more phosphonium ion ligand degradation products capable of reversion to useful ligand; (b) treating the reaction product fluid from step (a) with an inert gas, hydrogen, synthesis gas, or mixture thereof, under conditions sufficient to revert the one or more phosphonium ion ligand degradation products back to triorganophosphine ligand; (c) feeding the reaction product fluid from step (b), now containing reduced amounts of phosphonium ion ligand degradation products, to a vaporizer or an extractor for separation into a first phase containing reaction products, by-products, and intermediate products and a second phase containing transition metal-triorganophosphine ligand complex catalyst and optionally free triorganophosphine ligand; and (d) recycling the second phase containing the transition metal-triorganophosphine ligand complex catalyst and optionally free triorganophosphine ligand back to reaction process step (a).

In a final aspect, this invention provides for an integrated process for carbonylation of a polyunsaturated olefin comprising (a) contacting a polyunsaturated olefin with carbon monoxide, optionally, in the presence of hydrogen, alcohol, or water, and in the presence of a transition metal-triorganophosphine ligand complex catalyst and free triorganophosphine ligand, under process conditions sufficient to prepare a reaction product fluid comprising a transition metal-triorganophosphine ligand complex catalyst, optionally free triorganophosphine ligand, one or more reaction products, by-products, and/or intermediate products including an α,β-unsaturated aldehyde, ketone, ester, or acid, and one or more phosphonium ion ligand degradation product capable of reversion to useful ligand; (b) feeding the reaction product fluid to a vaporizer or an extractor for separation into a first phase containing reaction products, by-products, and/or intermediate products, and a second phase containing transition metal-triorganophosphine ligand complex catalyst, optionally free triorganophosphine ligand, and one or more phosphonium ion ligand degradation products; (c) treating the second phase from step (b) containing the transition metal-triorganophosphine ligand complex catalyst, optionally free triorganophosphine ligand, and phosphonium ion ligand degradation products with an inert gas, hydrogen, synthesis gas, or a mixture thereof, under conditions sufficient to revert the phosphonium ion ligand degradation products back to triorganophosphine ligand; and (d) recycling the treated phase containing the transition metal-triorganophosphine ligand complex catalyst and optional free ligand, now containing reduced amounts of phosphonium ion ligand degradation products, back to reaction process step (a).

The ligand degradation products referred to in this invention are produced, for example, in reaction processes wherein a polyolefin, preferably a diene or triene, is reacted in the presence of a transition metal-triorganophosphine ligand complex catalyst, and typically free triorganophosphine ligand, to form as a product, by-product, or intermediate product a conjugated functionalized olefin, such as a conjugated unsaturated aldehyde, ketone, ester, carboxylic acid, or nitrile. As used herein, the term "polyolefin" or its equivalent "polyunsaturated olefin" refers to an olefin containing a plurality of unsaturated carbon-carbon double bonds, for example, butadiene. By way of example, the ligand degradation products referred to in this invention may be produced in a reaction process wherein a polyunsaturated olefin is reacted with carbon monoxide, optionally, in the presence of hydrogen, alcohol, or water, and in the presence of a Group VIII transition metal-triorganophosphine ligand complex catalyst to form as a product, by-product, or intermediate product an α,β-unsaturated aldehyde, ketone, ester, or acid. Alternatively, the starting point for preparing the conjugated functionalized olefin may be an unconjugated functionalized olefin, for example, 3-alkenals, which may be prepared by the processes described herein or by alternative methods known to those of skill in the art. Such unconjugated functionalized olefins may be isomerized, for example, to the conjugated functionalized olefin, for example, 2-alkenals. The unconjugated and conjugated functionalized olefins may be isolated or not isolated from the reaction product fluids, depending upon the engineering design of those skilled in the art.

The following example illustrates one pathway by which the phosphonium ion ligand degradation product(s) may be formed; but the description herein should not be binding upon the invention in any manner. Specifically, the carbonylation of butadiene with carbon monoxide in the presence of hydrogen and a Group VIII transition metal-trialkylphosphine ligand complex catalyst produces 3-pentenal as a primary product, which in the reaction fluid can be isomerized to 2-pentenal. 3-Pentenal meets the requirements of the unconjugated functionalized olefin. The term "unconjugated" shall mean that the carbon-carbon double bond is separated from the functional group (for example, aldehyde, keto, ester, acid, or nitrile) by two or more carbon-carbon single bonds. In contrast, 2-pentenal meets the requirements of the conjugated functionalized olefin. The term "conjugated" shall mean that the carbon-carbon double bond is separated from the functional group by only one carbon-carbon single bond. Reaction of the triorganophosphine ligand and the conjugated functionalized olefin produces a phosphonium zwitter-ion that herein is referred to as the "phosphonium ion ligand degradation product." For example, the reaction of the α,β-unsaturated product 2-pentenal (I) with triorganophosphine ligand ($PR_3$) produces the zwitter-ionic phosphonium salt (II) shown hereinafter:

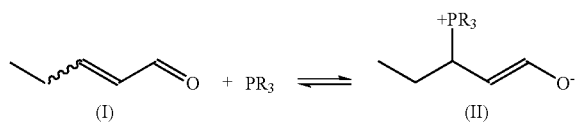

Analogous phosphonium ion ligand degradation products can be formed by the addition of a triorganophosphine ligand with a conjugated functionalized olefin having a different electron-withdrawing group, such as, ketone, ester, acid, or nitrile. Likewise, the conjugated functionalized olefin can have a similar or different chain length as compared with the pentyl chain shown in formula I.

More generally, the conjugated functionalized olefin may be represented by the following formula III:

wherein X is selected from the group consisting of formyl (—CHO), keto [—C(O)$R^4$)], ester [—COO$R^4$)], acid (—COOH), and nitrile (—CN); wherein each $R^1$, $R^2$, and $R^3$ is independently selected from hydrogen and monovalent hydrocarbon radicals, with the proviso that at least one of $R^1$, $R^2$, or $R^3$ is a monovalent hydrocarbon radical. Suitable monovalent hydrocarbon radicals include unsubstituted or substituted alkyl, cycloalkyl, and aryl radicals, having from 1 to 60 carbon atoms. Suitable substituents include alkyl, alkoxy, silyl, amino, acyl, carboxy, ether, halogen, and nitro radicals, and the like. $R^4$ is also a monovalent hydrocarbon radical, such as alkyl, cycloalkyl, or aryl, preferably, a $C_{1-20}$ monovalent hydrocarbon radical.

Reaction of the aforementioned conjugated functionalized olefin with triorganophosphine ligand produces phospho-nium ion ligand degradation products, which disadvantageously consume useful ligand, result in loss of catalytic metal and catalyst activity, and reduce product yields by catalyzing the formation of heavies. It is therefore an object of this invention to avoid phosphonium ion ligand degradation products, either by minimizing (including reducing, lessening, or lowering) the formation of such products during the reaction process itself or by reverting the ligand degradation products, already formed and present in reaction product fluids, back to useful ligands.

The reaction processes applicable to this invention may comprise any reaction wherein a polyolefin is converted, optionally in the presence of hydrogen and/or other co-reactants, and in the presence of a transition metal-triorganophosphine ligand complex catalyst to form as a product, by-product, or intermediate product a conjugated functionalized olefin. As noted hereinbefore, suitable functionalizations include formyl, ketone, ester, acid, and nitrile groups. Illustrative reaction processes include, for example, hydroformylation, hydroacylation, hydroesterification, carbonylation, and hydrocyanation.

Hydroformylation can be conducted in accordance with conventional procedures known in the art, and optionally, with the modifications disclosed herein. For example, unsaturated aldehydes can be prepared by reacting a polyolefin with carbon monoxide and hydrogen under hydroformylation conditions in the presence of a transition metal-triorganophosphine ligand complex catalyst.

Hydroacylation can be carried out in accordance with conventional procedures known in the art, and optionally, with the modifications disclosed herein. Unsaturated ketones can be prepared by reacting a polyolefin with carbon monoxide and hydrogen under hydroacylation conditions in the presence of a transition metal-triorganophosphine ligand complex catalyst. In this process unsaturated aldehyde typically forms as the initial product, which then reacts further with olefin to form an unsaturated ketone.

Hydroesterification can be carried out in accordance with conventional procedures known in the art, and optionally, with the modifications disclosed herein. For example, unsaturated esters can be prepared by reacting a polyolefin, carbon monoxide, and an alcohol under hydroesterification conditions in the presence of a transition metal-triorganophosphine ligand complex catalyst.

Carbonylation can be carried out in accordance with conventional procedures known in the art, and optionally, with the modifications disclosed herein. Unsaturated acids can be prepared by carbonylating a polyolefin with carbon monoxide in the presence of water and a transition metal-triorganophosphine ligand complex catalyst.

Hydrocyanation can be carried out in accordance with conventional procedures known in the art, and optionally, with the modifications disclosed herein. For example, unsaturated nitriles can be prepared by reacting a polyolefin with hydrogen cyanide under hydrocyanation conditions in the presence of a transition metal-triorganophosphine ligand complex catalyst.

A more preferred reaction process comprises carbonylation wherein a polyolefin (polyunsaturated olefin), preferably, a $C_{4-60}$ polyene ($C_{4-60}$ polyunsaturated olefin), is contacted with carbon monoxide and, optionally, hydrogen, alcohol or water, in the presence of a transition metal-triorganophosphine ligand complex catalyst, under conditions sufficient to form an α,β-unsaturated aldehyde, ketone, ester, or acid.

It is noted that the reactant polyunsaturated olefin need not necessarily be conjugated for one of the resulting products, by-products, or intermediate products to comprise a conjugated functionalized olefin. Unconjugated polyolefins may produce products having a carbon-carbon double bond in unconjugated relationship with an electron-withdrawing group; and such unconjugated products may isomerize under reaction process conditions to the conjugated functionalized olefin. (3-Pentenal, formed as an initial unsaturated aldehyde hydroformylation product, may be isomerized to 2-pentenal, as noted above.) Thus, the conjugated functionalized olefin may be formed as a primary product of the reaction process; or as a by-product via side reactions of the reactants or primary products; or as a relatively stable intermediate product of measurable concentration.

The reaction processes described hereinabove may employ any of the general processing techniques described in the prior art. The processes, for instance, can be conducted in either the liquid or gaseous states and in a continuous, semi-continuous or batch fashion, and may involve a liquid recycle and/or gas recycle operation or a combination of such systems, as desired. Likewise, the manner or order of addition of the reaction components is not critical and may be accomplished in any conventional fashion. As described hereinafter, the reaction processes can be modified by careful selection of triorganophosphine ligands, polyolefin conversion, and/or process conditions to minimize the formation of phosphonium ion ligand degradation products. The reaction product fluid resulting from any of the reaction processes described hereinabove is contemplated to include, but not limited to, a reaction fluid containing an amount of any one or more of the following: (a) a transition metal-triorganophosphine ligand complex catalyst; (b) free triorganophosphine ligand; (c) one or more reaction products, by-products, and/or intermediate products, including at least one compound comprising a conjugated functionalized olefin; (d) unconverted reactants, including polyolefin and/or unconjugated functionalized olefin; (e) optionally, an organic solubilizing agent or solvent for the complex catalyst, free triorganophosphine ligand, and any other components, as necessary; and (f) if not completely minimized during reaction processing, one or more phosphonium ion ligand degradation products. The separation of products, by-products, and intermediate products from the complex catalyst, optional free ligand, unconverted reactants, and any solvent or solubilizing agent may be effected by any known methods, preferably, the non-aqueous phase separation methods disclosed in U.S. Pat. Nos. 6,294,700 and 6,303, 829, or the aqueous liquid phase separation method disclosed in U.S. Pat. No. 5,180,854, or if appropriate, by standard vaporization; all patent citations being incorporated herein by reference.

The polyolefins, or alternatively, "polyunsaturated olefins" or "polyenes," that may be employed in the reaction processes described herein include, typically, organic compounds containing two or more carbon-carbon double bonds (unsaturated bonds). The double bonds may be conjugated or unconjugated. Such polyolefins can consist of straight-chain, branched chain or cyclic structures, with unsaturated bonds at internal or terminal positions. Mixtures of such polyolefins may also be employed. The polyolefins employed herein and the products correspondingly derived therefrom may also contain one or more substituents that do not unduly adversely affect the reaction process, the minimization process, and reversion process of this invention. Suitable substituents are described, for example, in U.S. Pat. Nos. 3,527,809 and 4,769,498, incorporated herein by reference. Substituents that may be suitably employed include hydroxy, nitrile, ester, acid, ketone, aldehyde, ether, halide, sulfoxide, sulfonic acid, sulfonate ester, amine, amide, aryl and substituted aryl functionalities. Accordingly, polyolefins suitable for the invention include, without limitation, butadiene, pentadienes, hexadienes, heptadienes, octadienes, dicyclopentadiene, hexatrienes, octatrienes, cyclooctadiene, 2,4-pentadienoic acid, 2,4-hexadienoic acid (sorbic), 2,4-decadienoic acid, 2,4-dodecadienoic acid, cis-9,cis-12-octadecadienoic acid (linoleic), trans-9,trans-12-octadecadienoic acid (linolelaidic), 5,6-octadecadienoic acid (laballenic), 5,13-docosadienoic acid, 6,10,14-hexadecatrienoic acid (hiragonic), cis-9, cis-12,cis-15-octadecatrienoic acid (linolenic), cis-9,trans-11,trans-13-octadecatrienoic acid ($\alpha$-eleostearic), trans-9, trans-11,trans-13-octadecatrienoic acid ($\beta$-eleostearic), and the like; as well as the mono-, di-, and tri-glycerol esters and the $C_{1-8}$ alkyl esters (methyl, ethyl, propyl, butyl, etc.) of the aforementioned carboxylic acids. Preferred classes of polyolefins include $C_{4-60}$ polyenes, such as, $C_{4-60}$ diolefins and triolefins. The most preferred polyolefins are selected from the group consisting of butadiene, sorbic acid, linoleic acid, linolenic acid, and the corresponding mono-, di-, and tri-glycerol esters and $C_{1-8}$ alkyl esters of the aforementioned acids. The above-noted glycerol and alkyl esters of long-chain carboxylic acids (for instance, fatty acids) may be derived from natural and genetically-modified oils including, for example, vegetable oils, seed oils, and fish oils. Non-limiting examples of such oils include soybean, castor, and canola oils, and the like.

The transition metal-triorganophosphine ligand complex catalyst may comprise any of the various known complex catalysts of this type, provided that they exhibit acceptable catalytic activity in the reaction process of interest. The transition metal is typically selected from the metals of Groups 8, 9 and 10 of the Periodic Table, and preferably selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium; and more preferably rhodium, cobalt and ruthenium; and most preferably, rhodium. Other permissible metals include Group 6 metals selected from chromium (Cr), molybdenum (Mo), tungsten (W) and mixtures thereof. Mixtures of metals from Groups 6, 8, 9 and 10 may also be used.

The term "complex" as used herein and in the claims means a coordination compound formed by the union of at least one triorganophosphine ligand with a transition metal. Carbon monoxide (which is also properly classified as a ligand) can also be present and complexed with the metal. The ultimate composition of the complex catalyst may also contain an additional ligand, for example, hydrogen or an anion satisfying the coordination sites or nuclear charge of the metal. Illustrative additional ligands include, for example, halogen (Cl, Br, I), alkyl, aryl, substituted aryl, acyl, $CF_3$, $C_2F_5$, CN, $(R^5)_2PO$ and $R^5P(O)(OH)O$ (wherein each $R^5$ is the same or different and is a substituted or unsubstituted hydrocarbon radical, for example, the alkyl or aryl), acetate, acetylacetonate, $SO_4$, $PF_4$, $PF_6$, $NO_2$, $NO_3$, $CH_3O$, $CH_2=CHCH_2$, $CH_3CH=CHCH_2$, $C_6H_5CN$, $CH_3CN$, $NH_3$, pyridine, $(C_2H_5)_3N$, mono-olefins, polyolefins and triolefins, tetrahydrofuran, and the like. The number of available coordination sites on the transition metal is well known in the art, and typically ranges from about 4 to about 6. The catalytic species may comprise a complex catalyst mixture in their monomeric, dimeric or higher nuclearity forms, which are preferably characterized by at least one triorganophosphine complexed per one molecule of metal, for example, rhodium. For instance, it is considered that the catalytic species of the complex catalyst employed in the preferred carbonylation reaction may be complexed with carbon monoxide in addition to triorganophosphine ligand. In hydroformylation processes employing both carbon monoxide and hydrogen gases, the catalytic species of the complex catalyst may include carbon monoxide and hydrogen.

Among the triorganophosphines that may serve as the ligand of the transition metal-ligand complex are trialkylphosphines, tricycloalkylphosphines, dialkylarylphosphines, alkyldiarylphosphines, dicycloalkylarylphosphines, cycloalkyldiarylphosphines, triaralkylphosphines, and triarylphosphines. Of course any of the hydrocarbon radicals of such tertiary triorganophosphines may be substituted if desired, with any suitable substituent that does not unduly adversely affect the desired result of the reaction. Triorganophosphine ligands suitably employed in the complex catalysts and reaction processes described hereinabove, as well as methods for these ligand preparations, are known in the art. As noted hereinafter, certain of these ligands may possess an advantaged steric or electronic property that minimizes the formation of phosphonium ion ligand degradation products.

Triorganophosphine ligands suitable for use in the reaction processes described herein may be represented by formula IV:

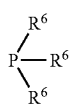

(IV)

wherein each $R^6$ is the same or different and is a substituted or unsubstituted monovalent hydrocarbon radical, for example, an alkyl or aryl radical. Suitable hydrocarbon radicals may contain from 1 to 24 carbon atoms or greater. Illustrative substituent groups that may be present on the aryl radicals include, for example, alkyl radicals, alkoxy radicals, silyl radicals such as —Si($R^7$)$_3$; amino radicals such as —N($R^7$)$_2$; acyl radicals such as —C(O)$R^7$; carboxy radicals such as —C(O)O$R^7$; acyloxy radicals such as —OC(O)$R^7$; amido radicals such as —C(O)N($R^7$)$_2$ and —N($R^7$)C(O)$R^7$; ionic radicals such as —SO$_3$M wherein M represents inorganic or organic cation; sulfonyl radicals such as —SO$_2R^7$; ether radicals such as —O$R^7$; sulfinyl radicals such as —SO$R^7$; sulfenyl radicals such as —S$R^7$ as well as halogen, nitro, cyano, trifluoromethyl and hydroxy radicals, and the like, wherein each $R^7$ individually represents the same or different substituted or unsubstituted monovalent hydrocarbon radical, with the proviso that in amino substituents such as —N($R^7$)$_2$, each $R^7$ taken together can also represent a divalent bridging group that forms a heterocyclic radical with the nitrogen atom and in amido substituents such as C(O)N($R^7$)$_2$ and —N($R^7$)C(O)$R^7$ each —$R^7$ bonded to N can also be hydrogen. Illustrative alkyl radicals include, for example, methyl, ethyl, propyl, n-butyl, iso-butyl, t-butyl, and the like. Illustrative cycloalkyl radicals include, for example, cyclohexyl. Illustrative aryl radicals include, for example, phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific triorganophosphines include, without limitation, for example, tri-iso-butylphosphine, cyclohexyl-di-n-butylphosphine, trioctylphosphine, triphenylphosphine, tris-p-tolyl phosphine, tris-p-methoxyphenylphosphine, tris-p-fluorophenylphosphine, tris-p-chlorophenylphosphine, tris-dimethylamino-phenylphosphine, propyldiphenylphosphine, t-butyldiphenylphosphine, n-butyl-diphenylphosphine, n-hexyldiphenylphosphine, cyclohexyldiphenylphosphine, dicyclohexylphenylphosphine, tricyclohexylphosphine, tribenzylphosphine, as well as the alkali and alkaline earth metal salts of sulfonated triphenylphosphines, for example, of (tri-m-sulfophenyl)phosphine, of (m-sulfophenyl)diphenyl-phosphine, and of dicyclohexylphenylphosphine monosulfonate, and the like. More particularly, illustrative metal-triorganophosphine complex catalysts and illustrative free triorganophosphine ligands include, for example, those disclosed in the following U.S. Pat. Nos. 3,527,809; 4,148,830; 4,283,562; 4,400,548; 6,369,283; and 5,886,237; the disclosures of which are incorporated herein by reference.

The metal-triorganophosphine ligand complex catalysts may be in homogeneous or heterogeneous form. For instance, preformed rhodium hydrido-carbonyl-triorganophosphine ligand catalysts may be prepared and introduced into the reaction fluid of a particular process. More preferably, the metal-triorganophosphine ligand complex catalysts can be derived from a catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction fluid along with the triorganophosphine ligand for the in situ formation of the active catalyst. As an example, rhodium dicarbonyl acetylacetonate or $Rh_4(CO)_{12}$ may be employed as a rhodium precursor and reacted in the presence of a solvent with the triorganophosphine ligand to form a catalytic rhodium-triorganophosphine ligand complex precursor which is introduced into the reaction zone along with excess (free) triorganophosphine ligand for the in situ formation of the active catalyst.

The amount of metal-triorganophosphine ligand complex catalyst present in the reaction medium need only be a minimum amount necessary to catalyze the particular process desired. In general, metal concentrations in the range of from about 1 part per million (ppm) to about 10,000 ppm, calculated as free metal, are suitably employed.

The concentration of the triorganophosphine ligand used in the reaction process is typically any amount greater than about 0.05 equivalent of the metal used. The upper limit depends on the solubility of the ligand and the amount of ligand needed to prevent deposition of the catalytic metal from the reaction medium. Typically, the reaction process, for example, the hydroformylation process, is carried out in the presence of free triorganophosphine ligand, so as to maintain catalytic metal in complexed form. An amount of ligand of from about 1.1 to about 200 moles per mole of metal (for example, rhodium) present in the reaction medium are suitable for most purposes, particularly with regard to rhodium catalyzed hydroformylation; the amount of ligand employed being the sum of both the amount of ligand that is bound (complexed) to the metal present and the amount of free (non-complexed) ligand present. While beneficially maintaining catalytic metal in complexed form, the excess triorganophosphine ligand is available, however, for detrimental reactions with α,β-unsaturated products, by-products, and intermediate products, for instance, conjugated functionalized olefins, to form phosphonium ion ligand degradation products.

The reaction conditions employable in reacting the polyunsaturated olefin to form products, including at least one conjugated functionalized olefin, depend upon the particular reaction under consideration. For each of the above-identified reaction processes, process conditions are described in the art, as found, for example, in Kirk-Othmer, *Encyclopedia of Chemical Technology*, Fourth Edition, 1996, the pertinent portions of which are incorporated herein by reference. Depending on the particular process, operating temperatures may range from about −80° C. or less to about 500° C. or greater and operating pressures can range from about 1 psig (6.9 kPa) or less to about 10,000 psig (69 MPa) or greater. The reaction time will normally be within the range of from about 30 minutes to about 200 hours, and preferably from less than about 1 hour to about 10 hours.

A preferred carbonylation process is hydroformylation. Illustrative transition metal-triorganophosphine ligand complex catalyzed hydroformylation processes include such processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; and 5,491,266; the disclosures of which are incorporated herein by reference. Process conditions described in these references may be suitably applied to the hydroformylation process described herein. Modifications of the disclosed processes, as mentioned hereinafter, may be employed to minimize phosphonium ion ligand degradation products. More specifically, the total gas pressure of hydrogen, carbon monoxide and polyolefin starting compound may range from about 1 psia (6.9 kPa) to about 10,000 psia (69 MPa). In general, however, it is preferred that the process be operated at a total gas pressure of hydrogen, carbon monoxide and polyunsaturated olefin starting compound of less than about 2,000 psia (13.8 MPa) and more preferably less than about 500 psia (3.5 MPa). The minimum total pressure is limited predominately by the amount of reactants necessary to obtain a desired rate of reaction. More specifically the carbon monoxide partial pressure of the hydroformylation process is preferably from about 1 psia (6.9 kPa) to about 1,000 psia (6,895 kPa), and more preferably from about 3 psia (21 kPa) to about 800 psia (5,600 kPa), while the hydrogen partial pressure is preferably about 5 psia (34.5 kPa) to about 500 psia (3,447 kPa) and more preferably from about 10 psia (69 kPa) to about 300 psia (2,068 kPa). In general $H_2$:CO molar ratio of gaseous hydrogen to carbon monoxide may range from about 1:10 to 100:1 or higher, the more preferred hydrogen to carbon monoxide molar ratio being from about 1:10 to about 10:1. Further, the hydroformylation process may be conducted at a reaction temperature from about −25° C. to about 200° C. In general hydroformylation reaction temperatures of about 50° C. to about 140° C. are preferred for polyolefinic starting materials.

In one aspect of this invention, the phosphonium ion ligand degradation product can be minimized by driving the conversion of polyunsaturated olefin or unconjugated functionalized olefin to a value greater than about 80 weight percent. For the purposes of this invention, the term "polyunsaturated olefin conversion" shall be defined as the weight percentage of polyunsaturated olefin that is fed to the reaction process and converted to products. For the purposes of this invention, the phrase "conversion of unconjugated functionalized olefin" shall be defined as the weight percentage of unconjugated functionalized olefin that is fed to the reaction process and converted to products. More specifically, the phosphonium ion ligand degradation products can be minimized by driving the aforementioned conversions to a value greater than about 80 weight percent, preferably, greater than about 85 weight percent, more preferably, greater than about 90 weight percent. In embodiments of the invention involving conversion of polyunsaturated olefins derived from seed oil feedstocks, the conversion is preferably less than about 95 weight percent, otherwise detrimental effects, for example, lowered selectivity or catalyst degradation, may occur.

Conversion can be driven to high values by manipulating process conditions, for example, by increasing reaction time, by selection of more active forms of the carbonylation catalyst, or by combinations of the above with variation in other process conditions, such as temperature and pressure. Higher temperatures may be employed to increase conversion; but temperature alone may not control the conversion. For instance, it may be advantageous to conduct the process at a lower temperature for a longer time to slow the rate of formation of phosphonium ion, while effecting high conversion. Typically, temperatures in excess of about 60° C., but less than about 180° C. are suitably employed for effecting high conversion. Typically, reaction times in excess of about 1 hour are suitably employed to effect high conversion, and preferably, greater than about 2 hours.

In another aspect of this invention, the phosphonium ion ligand degradation product can be minimized by selection of reaction conditions regardless of the conversion of polyunsaturated olefin or unconjugated functionalized olefin. Conditions affecting the rate of phosphonium ion formation include temperature and pressure. Typically, in order to minimize the phosphonium ion ligand degradation product(s) without concern for conversion, the reaction temperature is maintained at less than about 95° C., preferably less than about 85° C., and more preferably, less than about 75° C. Typically, however, the reaction temperature is greater than about 45° C. Typically, reaction pressure is greater than about 300 psig (2,068 kPa), preferably, greater than about 400 psig (2,758 kPa), and more preferably, greater than about 600 psig (4,137 kPa). Typically, however, reaction pressure is less than about 5,000 psig (34.5 MPa). As a general guideline, when using polyunsaturated olefins derived from seed oil feedstocks, the process conditions are preferably maintained as just mentioned hereinabove to minimize phosphonium ion formation, as opposed to operating to higher conversions of the polyunsaturated feedstock.

In another method of this invention, the phosphonium ion ligand degradation product(s) can be minimized by selection of triorganophosphine ligands with reduced nucleophilicity towards reaction with conjugated functionalized olefin product, by-product, or intermediate product. The nucleophilicity of the triorganophosphine ligand governs the rate of reaction to form phosphonium ion ligand degradation products. It is known that the nucleophilicity of phosphines is affected by both the steric and electronic properties of the phosphorus atom, and that these properties are determined by the nature of the groups bonded to the phosphorus. (For reference, see Wm. A. Henderson, Jr. and Sheldon A. Buckler, *Journal of the American Chemical Society*, (1960) 82, 5794-5800, incorporated herein by reference.) By selection of ligands having an advantaged steric or electronic property, formation of phosphonium ion ligand degradation products is minimized and, preferably, eliminated. Ligand cone angle and ligand basicity, as measured by pKa, often find use as estimates, respectively, of the steric and electronic properties of triorganophosphines. These effects are often confounded within a ligand or collection of ligands, so that it may be difficult to determine whether both or only one of these effects is responsible for reducing the nucleophilicity of a particular ligand. Nevertheless, the extent of formation of phosphonium ion ligand degradation products can be experimentally correlated with ligand cone angle or basicity, as measured by pKa.

"Ligand cone angle" and its method of measurement are described by Chadwick A. Tolman, in "Steric Effects of Phosphorus Ligands in Organometallic Chemistry and Homogeneous Catalysis," *Chemical Reviews,* 1977, 77(3), 313, incorporated herein by reference. In brief, the cone angle of a symmetrical phosphorus ligand (for instance, all three substituents the same) can be determined from a space-filling molecular model of the phosphorus compound by measuring the apex angle of a cylindrical cone centered at a distance corresponding to 2.28 Angstroms from the center of the phosphorus atom that just touches the van der Waals radii of the outermost atoms. If there are internal degrees of freedom in the molecule, such as rotation about the P—C bonds, the minimum cone angle is typically measured. For an unsymmetrical ligand, the cone angle is determined by summing the angles that each of the substituents subtend at a point corresponding to a distance of 2.28 Angstroms from the center of the phosphorus atom by the P—C vector and an outermost van der Waals contact for each of the three substituents. In general, the more sterically congested a triorganophosphine, the larger its cone angle, and the less nucleophilic the ligand. It has now been discovered that as the cone angle and hence steric bulk of the triorganophosphine ligand increase, the formation of phosphonium ion ligand degradation products decreases. Typically, to effect minimization of phosphonium ion ligand degradation products, a triorganophosphine ligand is employed having a ligand cone angle of greater than about 135°, preferably, greater than about 138°, and more preferably, greater than about 142°. Practically, the upper limit on ligand cone angle is about 230°, although in principle the cone angle may be higher. Non-limiting examples of triorganophosphine ligands having a ligand cone angle of greater than about 135° include tri-isopropylphosphine, tri-isobutylphosphine, tri-tertiarybutylphosphine, tricyclohexylphosphine, tri-n-octylphosphine, cyclohexyl-di-n-butylphosphine, tri(o-methylphenyl)phosphine, and tri-n-butylphosphine.

Basicity (electronic effect) measures the reactivity of a ligand towards a proton. Ligands with lower attraction to binding a proton are less basic, and therefore, generally of lower nucleophilicity. Ligands with lower basicity, and hence lower nucleophilicity, typically provide for slower and less extensive formation of phosphonium ion ligand degradation products. Generally, basicity is measured by pKa, known to those of skill in the art, as described in *Organometallics,* (1989) 8(1), 1, and by Wm. A. Henderson, Jr. and C. A. Streuli, *Journal of the American Chemical Society,* (1960), 82, 5791-5794, and by Tim Allman, et al., *Canadian Journal of Chemistry* (1982), 60(6), 716-722, all references incorporated herein by reference. Ligands having a pKa typically of less than about 8.3 provide for reduced formation of phosphonium ion ligand degradation products. Non-limiting examples of triorganophosphine ligands having a pKa of less than about 8.3 include tri-isobutylphosphine, dimethylphenylphosphine, methyldiphenylphosphine, and triphenylphosphine.

When the polyolefin or unconjugated functionalized olefin conversion is taken to a value greater than about 80 weight percent, or when the triorganophosphine ligand employed in the reaction process has a cone angle greater than about 135°, or a pKa less than about 8.3, then the total concentration of phosphonium ion ligand degradation product(s) in the reaction product fluid is typically less than about 10 weight percent, preferably, less than about 5 weight percent, more preferably, less than about 1 weight percent, and most preferably, less than about 0.1 weight percent, based on the total weight of phosphorus present. Moreover, the rate of ligand usage is typically less than about 2, preferably less than about 1, and more preferably less than about 0.1 gram ligand per liter reaction fluid per day.

In some instances, it may be difficult to drive the conversion of reactants to near completion without introducing other adverse effects on the process. Side reactions, for example, to form heavies or other undesirable by-products may increase at process conditions favorable to high conversion; and consequently, the selectivity to desired reaction products may decrease. Additionally, it may be difficult to select a triorganophosphine ligand that minimizes the formation of phosphonium ion ligand degradation products. For example, a ligand that provides optimal activity and selectivity to a particular desired product may not meet the criteria established herein for low nucleophilicity. Finally, it may be difficult to select reaction conditions that minimize the formation of phosphonium ion ligand degradation products and still meet all other performance targets. Consequently, the formation of phosphonium ion ligand degradation products may be unavoidable. In the above instances, it may be necessary to operate at lower conversion with the best ligand available for reaction purposes and/or at conditions which minimize capital investment, with the understanding that phosphonium ion ligand degradation products are likely to be formed. After the reaction is complete, the reaction product fluid can be treated to revert the ligand degradation product or products substantially back to useful triorganophosphine ligand.

Thus, in another aspect, this invention provides for the reversion of phosphonium ion ligand degradation product or mixture of such degradation products by treating the reaction product fluid containing one or more ligand degradation products with an inert gas, hydrogen, synthesis gas, or a combination thereof, under conditions sufficient to revert the phosphonium ion ligand degradation product or mixture of products back to useful triorganophosphine ligand. This method is operable when the phosphonium ion ligand degradation product is capable of reversion, and operates under the hypothesis that the phosphonium ion ligand degradation product resides in the reaction product fluid in equilibrium with its component parts: the triorganophosphine ligand and the conjugated functionalized olefin. Accordingly, removal of the conjugated functionalized olefin may result in a backwards shift in the equilibrium (reversion) towards triorganophosphine ligand. Such a hypothesis should not, however, be limiting or binding upon the invention in any manner. Since the reversion process invention is simple to execute, a simple test run in accordance with the invention can determine whether the phosphonium ion is capable of reversion.

Reversion treatment methods include sparging, stripping, and stirring, and any other technique that functions to contact adequately the reaction product fluid with the treatment gas. Typical inert gases include nitrogen, argon, helium, methane, carbon monoxide, steam, and mixtures thereof; preferably, nitrogen or carbon monoxide, and mixtures thereof. (Under the treatment conditions described herein, carbon monoxide and steam are substantially inert with respect to the components of the reaction product fluid.) Alternatively, molecular hydrogen or synthesis gas ($H_2$+CO) may be used as the treatment gas. Any syngas mixture will suffice, but preferred CO/$H_2$ molar ratios range from about 10/1 to about 1/10. Any mixture of inert gas, hydrogen, and syngas may be suitably employed. The treatment temperature during reversion may be any temperature ranging from room temperature to just below the temperature at which detrimental effects are evidenced on the catalyst, reactants, or products. Typically, the reversion treatment is conducted at a temperature greater than about 50° C., preferably, greater than about 70° C. Typically, the reversion treatment is conducted at a temperature less than about 150° C., and preferably, less than about 120° C. Typically, the reversion treatment is conducted at a pressure ranging from about sub-atmospheric to the pressure of the reaction process. Preferably, the reversion pressure ranges from about 0.01 psia (0.0689 kPa) to about 2000 psia (14 MPa), more preferably, from about 0.1 psia (0.689 kPa) to about 1000 psig (7 MPa). Reversion treatment time can vary depending upon the species and concentrations of phosphonium ion ligand degradation products present in the reaction product fluid. Typically, treatment time ranges from about 1 minute to about 1 hour, preferably, from about 5 minutes to about 30 minutes.

In a preferred embodiment, the reaction product fluid containing one or more phosphonium ion ligand degradation products is treated with an inert gas under conditions sufficient to volatize the conjugated functionalized olefin product or mixture of such products, thereby reverting the phosphonium ion ligand degradation product or products back to useful triorganophosphine ligand or mixture of useful ligands. This method is particularly suitable for application wherein the conjugated functionalized olefin, such as 2-pentenal, has substantial volatility at pressures and temperatures benign to other components of the reaction product fluid.

In another preferred embodiment, this invention comprises treating a reaction product fluid containing the phosphonium ion ligand degradation product with a source of hydrogen under conditions sufficient to hydrogenate the conjugated functionalized olefin. According to the hypothesis, which should not limit the invention in any manner, by such hydrogenation the equilibrium may be shifted backwards towards triorganophosphine ligand. The hydrogenation product behaves as an essentially inert compound in the carbonylation or hydroformylation reaction product fluid and is therefor not as problematical as its unsaturated counterpart in forming heavies by-products. This hydrogenation method is particularly suitable in those instances wherein the conjugated functionalized olefin has low volatility and cannot be removed by stripping methods.

In another preferred embodiment, this invention comprises treating a reaction product fluid containing the phosphonium ion ligand degradation product with a source of syn-gas under conditions sufficient to hydroformylate the conjugated functionalized olefin. According to the hypothesis, which should not limit the invention in any manner, by such hydroformylation the equilibrium may be shifted backwards towards triorganophosphine ligand. In some systems, the hydroformylation product of the conjugated functionalized olefin is very similar to the major desired product and is not problematic. This hydroformylation method is particularly suitable in those instances wherein the conjugated functionalized olefin has low volatility or wherein the olefin is not readily hydrogenated.

In practical terms, the reversion treatment of the reaction product fluid can be integrated into the reaction process, product separation, and catalyst recovery scheme in a variety of ways. In one embodiment, the reaction product fluid obtained from the process reactor and comprising the transition metal-triorganophosphine ligand complex catalyst, optional free triorganophosphine ligand, unconverted reactants, optional organic solubilizing agent or solvent, and one or more reaction products, by-products, and/or intermediate products, including at least one compound comprising a conjugated functionalized olefin, and one or more phosphonium ion ligand degradation products capable of reversion, can be fed to reversion unit (for example, inert gas stripper, or hydrogenator, or hydroformylator), wherein treatment is conducted to reverse the formation of phosphonium ion ligand degradation products. The effluent from the reversion unit, comprising the reaction product fluid containing reduced amounts of phosphonium ion ligand degradation products, may thereafter be fed to a first vaporizer to remove volatile products, by-products, and intermediate products, or alternatively, to an extractor for separation into a first phase comprising the products, by-products, and intermediate products and a second phase comprising the transition metal-triorganophosphine ligand complex catalyst and optionally free triorganophosphine ligand. Any reaction solvent and/or solubilizing agent may separate with the first or second phase depending upon their polarities with respect to the other components of the reaction product fluid. The phase containing the catalyst, optionally free ligand, and optionally solvent and/or solubilizing agent may be sent to a second vaporizer to remove any extraction solvent and then recycled back to the process reactor. Methods are known in the art for product separations, product recovery, and catalyst/ligand recycle.

In an alternative embodiment, the reaction product fluid from the process reactor may be fed to a first vaporizer to remove volatile products, or alternatively, to an extractor for separation into a first phase comprising the reaction products, by-products, and intermediate products and a second phase comprising the transition metal-triorganophosphine ligand complex catalyst, optionally free triorganophosphine ligand, and phosphonium ion ligand degradation products. Thereafter, the second phase containing the complex catalyst, optional free ligand, and phosphonium ion ligand degradation products capable of reversion may be fed to reversion unit (for example, inert gas stripper, hydrogenator, or hydroformylator), which serves to remove the phosphonium ion ligand degradation products by reversion back to useful ligand. The effluent from the reversion unit containing the complex catalyst and free ligand, now containing reduced amounts of ligand degradation products, may then be fed to a second vaporizer to remove any extraction solvent, and thereafter recycled to the process reactor. Again, the handling of the reaction solvent and/or solubilizing agent will depend upon the specifics of the extraction process and the polarities of the solvent and solubilizing agent relative to the other components of the reaction product fluid.

For illustrative purposes, the following examples are provided hereinafter of the various aspects of this invention; but the invention described herein should not be limited in any manner by these illustrative examples. One skilled in the art will recognize and appreciate variations of the illustrative examples that fall within the spirit and scope of the invention.

EXAMPLE 1

Reversion of Phosphonium Ion Ligand Degradation Products by Running Hydroformylation Process to Complete Conversion of Polyolefin A batch hydrocarbonylation of 1,3-butadiene (BD) to pentenols was conducted at the following conditions: 70° C., 300 psig (2,068 kPa) carbon monoxide, 600 psig (4,136 kPa) hydrogen, 1570 ppm Rh, 4.6 mol ligand/mol Rh, and 40 wt % initial BD in 1-butanol solvent. Trioctylphosphine was used as ligand, and the Rh source was $Rh_4(CO)_{12}$. Multiple samples were taken from the reactor and analyzed by phosphorus-31 nuclear magnetic resonance spectroscopy ($^{31}$P-NMR) to follow the concentration of phosphonium ion ligand degradation products (phosphonium salts) with time. The concentration of phosphonium salts increased between t=0 and t=60 min, and their concentration reached a maximum of 0.008 mol/L at t=60 min. During this same period, the concentration of ligand gradually decreased by 0.008 mol/L from its initial value. The concentration of 2-pentenal (α,β-unsaturated aldehyde) also reached a maximum at 60 min.

The BD conversion at the time when the concentrations of phosphonium salts and α,β-unsaturated aldehyde were at their maximum was 39%. Had the reaction been stopped at 39% conversion of BD, the ligand usage (lost) to phosphonium salts would have been 65 g/L/day. However, the reaction was continued until 480 minutes to allow for the 2-pentenal to react away under normal reaction conditions. The concentration of the 2-pentenal gradually decreased between t=60 min and t=480 min to a value that was about ten to almost twenty times less than its maximum value. The concentration of phosphonium salts also gradually decreased between t=60 and t=480 min, and their concentration was 0.0005 mol/L at t=480 min. During this same time period, the concentration of trioctylphosphine ligand gradually increased back to very near its original concentration indicating that reversion back to useful ligand had occurred. The BD conversion at t=480 min was 98%. When the reaction was stopped at 98% BD conversion, the ligand usage (lost) to phosphonium salts was less than 1 g/L/day.

EXAMPLE 2

Reversion of Phosphonium Ion Ligand Degradation Products by Reacting α,β-Unsaturated Aldehyde with Hydrogen A batch hydrocarbonylation of 1,3-butadiene (BD) was conducted to partial conversion followed by stripping of the reaction product solution with hydrogen to hydrogenate residual α,β-unsaturated aldehyde (2-pentenal). The batch hydrocarbonylation was conducted at the following conditions: 70° C., 300 psig (2,068 kPa) carbon monoxide, 600 psig (4,136 kPa) hydrogen, 1590 ppm Rh, 4.5 mol ligand/mol Rh, and 40 wt % initial BD in 1-butanol solvent. The ligand used was trioctylphosphine, and the Rh source was $Rh_4(CO)_{12}$. The reaction was conducted for 130 minutes and reached 67% conversion BD. At that time, the concentration of phosphonium salts and α,β-unsaturated aldehyde (2-pentenal) were both about 0.006 mol/L. If no attempt had been made to revert the phosphonium salts at this point, the ligand usage (lost) to phosphonium salts would have been 25 g/L/day. The reactor was vented down to atmospheric pressure to remove most of the syn-gas ($CO+H_2$). The reactor was then re-pressurized back to 900 psig (6,205 kPa) with pure hydrogen. The temperature was also increased to 120° C. Hydrogen was continuously sparged through the reactor at a rate of 0.5 standard cubic feet per hour (SCFH) during the time when the reactor was at 120° C. and 900 psig (6,205 kPa). After 10 minutes of stripping with hydrogen, all phosphonium salts were undetectable by $^{31}$P-NMR, and the α,β-unsaturated aldehyde was undetectable by gas chromatography. The concentration of both of these species remained at essentially "0" for the remainder of the experiment. The ligand usage (loss to phosphonium salts) was reduced from 25 g/L/day to less than 1 g/L/day by reverting the phosphonium salts by hydrogenating the residual α,β-unsaturated aldehyde with hydrogen.

EXAMPLE 3

Reversion of Phosphonium Ion Ligand Degradation Products by Removing α,β-Unsaturated Aldehyde by Stripping with an Inert Gas A batch hydrocarbonylation of 1,3-butadiene (BD) was conducted to partial conversion followed by stripping of the reaction product solution with nitrogen to remove residual α,β-unsaturated aldehyde (2-pentenal) by volatilization at high pressure. The batch hydrocarbonylation was conducted at the following conditions: 70° C., 300 psig (2,068 kPa) carbon monoxide, 600 psig (4,136 kPa) hydrogen, 1590 ppm Rh, 4.6 mol ligand/mol Rh, and 40 wt % initial BD in 1-butanol solvent. The ligand used was trioctylphosphine, and the Rh source was $Rh_4(CO)_{12}$. The reaction was conducted for 120 minutes and reached 72% conversion of BD. At that time, the concentration of phosphonium salts and α,β-unsaturated aldehyde were about 0.005 and 0.016 mol/L, respectively. If no attempt had been made to revert the phosphonium salts at this point, the ligand usage (lost) to phosphonium salts would have been about 20 g/L/day. The reactor was vented down to atmospheric pressure to remove most of the syn-gas. The reactor was then re-pressurized back to 900 psig (6,205 kPa) with pure $N_2$. The temperature was also increased to 120° C. Nitrogen was continuously sparged through the reactor at a rate of 0.5 SCFH during the time when the reactor was at 120° C. and 900 psig (6,205 kPa). After 20 minutes of stripping with nitrogen, the phosphonium salts had decreased to a concentration of 0.0005 mol/L but remained at about that level for the remainder of the experiment. The concentration of α,β-unsaturated aldehyde (2-pentenal) decreased from 0.016 to 0.005 mol/L during the first 20 minutes of stripping with $N_2$. However, the concentration of the phosphonium salts and the α,β-unsaturated aldehyde remained at the above-mentioned values for the remainder of the experiment. Accordingly, the phosphonium salts were partially, but not fully, reverted back to useful ligand when stripping with nitrogen. The ligand usage (loss to phosphonium salts) was reduced from 20 g/L/day to 2 g/L/day by reverting the phosphonium salts by stripping away much of the residual α,β-unsaturated aldehyde with nitrogen.

EXAMPLE 4

Minimization of Phosphonium Ion Ligand Degradation Products Through Ligand Selection In a series of hydroformylation reactions (4A-D) 2-pentenal (50 mmols) was subjected to hydrocarbonylation conditions for 3 hours using a rhodium catalyst promoted with a variety of ligands having different cone angles and pKa's. Hydrocarbonylation conditions included: 70° C., 300 psig (2,068 kPa) carbon monoxide, 600 psig (4,136 kPa) hydrogen, 1570 ppm Rh, 4.6 mol ligand/mol Rh, and 40 wt % initial 2-pentenal in 1-butanol solvent. The source of Rh was $Rh_4(CO)_{12}$. During the course of the reaction 2-pentenal was hydrogenated to valeraldehyde and then to pentanol. After the reaction was completed, the reaction fluid was examined by $P^{31}$-NMR spectroscopy to determine the amount of ligand converted to phosphonium ion ligand degradation product, as a percentage of the total ligand in solution. Results are shown in Table 1.

TABLE 1

Phosphonium Ion Ligand Degradation Product as a Function of Ligand Cone Angle and pKa

| Ex. 4 | Ligand | % Phosphonium Salt (by wt.) | Cone Angle (°) | PKa |
|---|---|---|---|---|
| 4A (comparative) | tri-n-butylphosphine | 16.8 | 132 | 8.43 |

TABLE 1-continued

Phosphonium Ion Ligand Degradation Product as a Function of Ligand Cone Angle and pKa

| Ex. 4 | Ligand | % Phosphonium Salt (by wt.) | Cone Angle (°) | PKa |
|---|---|---|---|---|
| 4B (comparative) | tri-n-octylphosphine | 17.9 | 132 | 8.3 (est*) |
| 4C (example) | Cyclohexyldi-n-butylphosphine | 9.8 | 145 | 8.9 (est*) |
| 4D (example) | Tri-isobutylphosphine | 0.3 | 143 | 7.97 |

*est = estimated value

It is seen from Table 1 in the comparative runs A and B, that tri-n-butylphosphine and tri-n-octylphosphine, both having a cone angle of 132° and a pKa of 8.3 or greater than 8.3, produced greater than 15 weight percent total ligand converted to phosphonium ion ligand degradation product. In contrast, it is seen in Table 1, example C, that cyclohexyldi-n-butyl phosphine having a cone angle of 145° produced only about sixty percent of the amount of ligand degradation product as compared with runs A and B. It is further seen in Table 1, example D, that tri-isobutylphosphine having a cone angle of greater than 135° and a pKa of less than 8.3 produced less than 1 weight percent phosphonium ion ligand degradation product. Moreover, as steric bulk increased and basicity decreased from cyclohexyldi-n-butylphosphine to tri-isobutylphosphine, the percentage of ligand degradation product decreased significantly, from 9.8 percent to only 0.3 percent. Accordingly, in view of the results, examples 4C and 4D illustrate the claimed invention, whereas experiments 4A and 4B are provided for comparative purposes.

Comparative Experiment 5

The hydroformylation of soy oil methyl esters was conducted at 100° C. for comparative purposes to illustrate the effect of temperature on the formation of ligand degradation products. Under a nitrogen atmosphere, a hydroformylation catalyst solution was prepared containing Ligand A (2.208 g, 5.866 mmol, initial ligand concentration in the reactor: 0.10M), Rh(CO)$_2$acac (0.0366 g, 0.142 mmol), and 1-methyl-2-pyrrolidone (NMP, 16.05 g). Ligand A, the monosulfonated sodium salt of bis(dicyclohexyl)phenylphosphine, has the following structure.

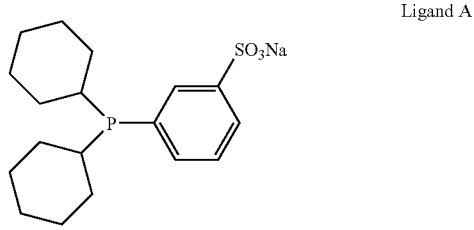

Ligand A

Also prepared under nitrogen was a neat solution of soybean oil-derived methyl esters (33.95 g, 115.08 mmol), prepared by the transesterification of soybean oil with methanol using standard methods known in the art. Soybean oil contains polyunsaturated esters. Under nitrogen, the catalyst solution was added into a 100 mL stainless steel reactor, and the soy methyl esters were added into a substrate delivery cylinder attached to the reactor. Both the reactor and the substrate delivery cylinder were purged three times with a gaseous mixture of carbon monoxide and hydrogen (CO:H$_2$=1:1 vol/vol) at 200 psig (1,379 kPa) pressure. The reactor was then sealed, stirred, and heated under the CO—H$_2$ gas mixture at 200 psig (1,379 kPa) pressure. When the catalyst solution reached 100° C., the soy methyl ester sample was forced into the reactor with the CO—H$_2$ gas mixture at 500 psig (3,447 kPa) pressure. The reactor was then fed with the CO—H$_2$ mixture at 500 psig (3,4447 kPa) for 15 minutes. The pressure in the reactor was then reduced to 30 psig (207 kPa). A gas chromatographic (GC) sample was taken to determine the concentration of total unsaturated aldehydes. The reaction was continued at 100° C. and 30 psig (207 kPa) and sampled for GC and phosphorus nuclear magnetic resonance spectroscopy ($^{31}$P NMR) at 24 and 96 hours. The average rate of phosphonium ligand degradation product formation was determined using the NMR data. Overall results are shown in Table 2.

TABLE 2

(Comparative Experiment 5) Phosphonium Ligand Degradation Product Formation at 100° C.

| Reaction Time (days) | Total unsaturated aldehyde (conjugated + unconjugated) (Mol/L) | Unsaturated Aldehyde consumption rate (Mol/L/day) | Phosphonium formation rate (Average g/L/day) |
|---|---|---|---|
| 0 | 0.414 | N/A | N/A |
| 4 | 0.309 | 0.026 | 0.1 |

NA = not applicable.

EXAMPLE 5

Minimization of Ligand Degradation Products as a Function of Temperature

The hydroformylation of soy oil methyl esters was conducted at 85° C. as an example of the invention to illustrate the effect of temperature on the formation of ligand degradation products. The procedure described in Comparative Experiment 5 was repeated with the following modifications. The reactor was charged with a catalyst solution containing Ligand A (4.40 g, 11.68 mmol, initial ligand concentration in the reactor: 0.14 M), Rh(CO)$_2$acac (0.0753 g, 0.292 mmol) and 30.0 g 1-methyl-2-pyrrolidone (NMP). The substrate delivery cylinder was charged with a neat solution of soybean oil derived methyl esters (45.01 g, 152.58 mmol). Both the reactor and the substrate delivery cylinder were purged three times with a gaseous mixture of carbon monoxide and hydrogen (CO:H$_2$=1:1 vol/vol) at 200 psig (1,379 kPa) pressure. The reactor was then sealed, stirred and heated under the gaseous mixture at 200 psig (1,379 kPa) pressure. When the solution reached 85° C., the soy methyl ester sample was forced into the reactor using the CO—H$_2$ gas mixture at 600 psig (4,137 kPa) pressure. The reactor was then fed with the CO—H$_2$ mixture for 30 min at 600 psig (4,137 kPa). The pressure in the reactor was reduced to 30 psig (207 kPa). GC samples were taken at this time to determine the concentration of total unsaturated aldehydes. The reaction was continued at 85° C. under 30 psig (207 kPa) CO—H$_2$ gas mixture and sampled for GC and $^{31}$P NMR at 67.6, 91.6 and 115.6 hours. The average rate of phosphonium ligand degradation product formation was determined using the NMR data. Results are shown in Table 3.

TABLE 3

| Reaction Time (days) | Phosphonium Ion Ligand Degradation Product Formation at 85° C. | | |
|---|---|---|---|
| | Total unsaturated aldehyde (conjugated + unconjugated) (Mol/L) | Unsaturated Aldehyde consumption rate (Mol/L/day) | Phosphonium formation rate Average (g/L/day) |
| 0 | 0.412 | N/A | N/A |
| 4 | 0.322 | 0.024 | 0.04 |

N/A = not applicable.

Comparing the results of Comparative Experiment 5 with Example 5, it is seen that the phosphonium formation rate was increased at 100° C. relative to the formation rate at 85° C. Given the fact that the concentration of Ligand A was greater in the sample run at 85° C. than in the sample run at 100° C., and that the formation of phosphonium is proportional to the concentration of ligand in solution, the lower formation rate at 85° C. shows that a temperature less than 100° C. minimizes the formation rate of phosphonium degradation products.

EXAMPLE 6

Minimization of Ligand Degradation Products as a Function of CO—$H_2$ Pressure

The formation rate of phosphonium degradation products was measured in a continuous hydroformylation mini-plant, which consisted of a reaction system comprised of three reactors in series and a product/catalyst separation system with catalyst recycle. The reactors were charged with a catalyst solution containing Ligand A (2.5 wt %) shown in Example 5 hereinabove, Rh(CO)$_2$acac (500 ppm Rh), and 20 wt % 1-methyl-2-pyrrolidone (NMP). A mixture of soy methyl esters was fed continuously to the first reactor. The reactors were operated at 600 psig (4,137 kPa) pressure by continuously feeding a gaseous mixture of carbon monoxide and hydrogen (CO:$H_2$=1:1 vol/vol). The reaction was conducted for 153 hours continuously at 85° C. The formation rate of phosphonium degradation products was measured to be 0.02 g/liter/day during this period. The pressure of carbon monoxide and hydrogen (CO:$H_2$=1:1 vol/vol) was then reduced to 400 psig (2,758 kPa) while keeping the temperature and other conditions unchanged. The reaction was conducted for 59 hours, and the formation rate of phosphonium degradation products was measured to be 0.03 g/liter/day during this period. The results illustrate a low rate of phosphonium formation at a pressure greater than 300 psig, and further that phosphonium formation decreases with increasing pressure.

EXAMPLE 7

Minimization of Ligand Degradation Products as a Function of Temperature

The formation rate of phosphonium degradation products was measured in a continuous hydroformylation mini-plant similar to the system described in Example 6. The reaction system was charged with a catalyst solution containing Ligand A (2.5 wt %) as shown in Example 5 hereinabove, Rh(CO)$_2$acac (500 ppm Rh), and 20 wt % 1-methyl-2-pyrrolidone (NMP). Soy methyl esters were fed continuously to the reaction system. The reactors were operated at 400 psig (2,758 kPa) pressure by continuously feeding a gaseous mixture of carbon monoxide and hydrogen (CO:$H_2$=1:1 vol/vol). The reaction was conducted continuously for 59 hours with all reactors at 85° C. The formation rate of phosphonium degradation products was measured to be 0.03 g/liter/day during this period.

Comparative Experiment 6

For comparative purposes, Example 7 was repeated with the exception that the temperature of the last reactor was increased to 100° C. while keeping the temperature of all other reactors at 85° C. All other conditions remained unchanged. The reaction was conducted for 140 hours and the formation rate of phosphonium degradation products was measured to be 0.07 g/liter/day during this period. The data illustrate that when all of the reactors were maintained at a temperature less than 95° C., the formation rate of phosphonium degradation products was significantly lower, as compared to the comparative experiment wherein even one reactor was maintained above 95° C.

EXAMPLE 8

Minimization of Ligand Degradation Products as a Function of Temperature and Pressure The formation rate of phosphonium degradation products was measured in a continuous hydroformylation mini-plant similar to the one described in Example 6. The reaction system was charged with a catalyst solution containing Ligand A (2 wt %), Rh(CO)$_2$acac (300 ppm Rh), and 30 wt % 1-methyl-2-pyrrolidone (NMP). Soy methyl esters, were fed continuously to the reaction system. The reactors were operated at 300 psig (2,068 kPa) pressure by continuously feeding a gaseous mixture of carbon monoxide and hydrogen (CO:$H_2$=1:1 vol/vol). The reaction was conducted continuously for 150 hours at 95° C. The formation rate of phosphonium degradation products were measured to be 0.05 g/liter/day during this period. The pressure of the reaction system was increased to 600 psig (4136 kPa), and the temperature of the reaction system was decreased to 85° C., while keeping all other conditions unchanged. The reaction was conducted for 350 hours and the formation rate of phosphonium degradation products was measured to be 0.02 g/liter/day during this period. The lower formation rate at 600 psig syn-gas pressure and 85° C. shows that a combination of higher pressure and lower temperature significantly minimizes the formation rate of phosphonium ion degradation products.

What is claimed is:

1. A method of minimizing the production of one or more phosphonium ion ligand degradation products in a process wherein an ester-substituted polyunsaturated olefin comprising an ester of a $C_{1-8}$ alkanol or glycerol is hydroformylated with carbon monoxide and hydrogen in the presence of a transition metal-triorganophosphine ligand complex catalyst to form as a product, by-product, or intermediate product an α,β-unsaturated aldehyde which is capable of forming a phosphonium ion ligand degradation product by reaction with the triorganophosphine ligand, the method comprising conducting the hydroformylation process with a triorganophosphine ligand having a ligand cone angle greater than 135°, or having a pKa of less than 8.3, or having both a ligand cone angle greater than 135° C. and a pKa less than 8.3, so as to minimize the formation of phosphonium ion ligand degradation product(s) such that the rate of ligand usage is less than about 0.1 gram ligand per liter reaction fluid per day.

2. The method of claim 1 wherein the triorganophosphine ligand having both a ligand cone angle greater than 135° C. and a pKa less than 8.3 is employed.

3. The method of claim 1 wherein the ester-substituted polyunsaturated olefin is selected from $C_{1-8}$ alkanol esters and the mono-, di-, and tri-glycerol esters of the following polyunsaturated carboxylic acids: 2,4-hexadienoic acid (sorbic), 2,4-decadienoic acid, 2,4-dodecadienoic acid, cis-9,cis-12-octadecadienoic acid (linoleic), trans-9,trans-12-octadecadienoic acid (linolelaidic), 5,6-octadecadienoic acid (laballenic), 5,13-docosadienoic acid, 6,10,14-hexadecatrienoic acid (hiragonic), cis-9,cis-12,cis-15-octadecatrienoic acid (linolenic), cis-9,trans-11,trans-13-octadecatrienoic acid (α-eleostearic), and trans-9,trans-11,trans-13-octadecatrienoic (β-eleostearic), and mixtures thereof.

4. The method of claim 1 wherein the ester-substituted polyunsaturated olefin comprises the methyl ester of cis-9,cis-12-octadecadienoic acid (linoleic), trans-9,trans-12-octadecadienoic acid (linolelaidic), 5,6-octadecadienoic acid (laballenic), 6,10,14-hexadecatrienoic acid (hiragonic), or cis-9,cis-12,cis-15-octadecatrienoic acid (linolenic).

5. The method of claim 1 wherein the ester-substituted polyunsaturated olefin is derived from natural and genetically-modified oils.

6. The method of claim 5 wherein the oils are selected from soybean, castor, and canola oils.

7. The method of claim 1 wherein the ester-substituted polyunsaturated olefin is hydroformylated to a conversion greater than about 80 weight percent and less than about 95 weight percent.

8. The method of claim 1 wherein the hydroformylation temperature is greater than about 45° C. and less than about 95° C.

9. The method of claim 1 wherein the hydroformylation total pressure is greater than about 300 psig and less than about 5,000 psig.

10. The method of claim 1 wherein the triorganophosphine ligand is selected from tri-isopropylphosphine, tri-isobutylphosphine, tri-t-butylphosphine, tricyclohexylphosphine, cyclohexyl-di-n-butylphosphine, trioctylphosphine, t-butyldiphenylphosphine, n-butyl-diphenylphosphine, n-hexyldiphenylphosphine, cyclohexyldiphenylphosphine, tri(o-methylphenyl)-phosphine, methyldiphenylphosphine, propyldiphenylphosphine, dimethylphenylphosphine, dicyclohexylphenylphosphine, triphenylphosphine, the alkali and alkaline earth metal salts of the aforementioned ligands substituted with one or more sulfonate ions, and mixtures of the aforementioned compounds.

11. The method of claim 10 wherein the triorganophosphine ligand is the sodium salt of dicyclohexylphenyl phosphine monosulfonate.

12. The method of claim 11 wherein the ester-substituted polyunsaturated olefin comprises one or more $C_{1-8}$ alkanol esters of soy oil or one or more mono,- di-, and/or triglyceride esters of soy oil.

* * * * *